United States Patent [19]

Sutherland et al.

[11] Patent Number: 4,818,710
[45] Date of Patent: * Apr. 4, 1989

[54] METHOD FOR OPTICALLY ASCERTAINING PARAMETERS OF SPECIES IN A LIQUID ANALYTE

[75] Inventors: Ranald M. Sutherland, Geneva; Claus Dähne; Georges Revillet, both of Onex, all of Switzerland

[73] Assignee: Prutec Limited, United Kingdom

[*] Notice: The portion of the term of this patent subsequent to Oct. 4, 2005 has been disclaimed.

[21] Appl. No.: 805,903

[22] Filed: Dec. 6, 1985

[30] Foreign Application Priority Data

Dec. 10, 1984 [EP] European Pat. Off. ........ 84810600.1

[51] Int. Cl.$^4$ .................. G01N 21/00; G01N 33/552; G01N 33/72
[52] U.S. Cl. ........................... 436/527; 250/227; 250/302; 250/365; 356/445; 422/57; 422/58; 422/68; 436/67; 436/165; 436/172; 436/805
[58] Field of Search ................ 436/805, 67, 165, 172, 436/527; 250/227, 302, 365; 422/57, 68, 58

[56] References Cited

U.S. PATENT DOCUMENTS

| | | | |
|---|---|---|---|
| 4,399,099 | 8/1983 | Buckles | 436/805 |
| 4,451,434 | 5/1984 | Hart | 422/102 |
| 4,558,014 | 12/1985 | Hirschfeld | 436/527 |
| 4,582,809 | 4/1986 | Block | 436/805 |
| 4,654,532 | 3/1987 | Hirschfeld | 436/527 X |
| 4,671,938 | 6/1987 | Cook | 436/527 X |

Primary Examiner—Sidney Marantz
Attorney, Agent, or Firm—Cushman, Darby & Cushman

[57] ABSTRACT

An optical waveguide with one or more coatings of reactants specific to species to be analyzed in a liquid analyte immersed therein. A light signal carried by the waveguide undergoes interaction either with the bulk analyte whereby a first signal in connection with the bulk analyte is obtained and, simultaneously, with a layer of complex resulting from the reaction of one of said specific reactant with one of said species or with two or more complex layers corresponding to two or more of said species, this generating a second (or more) signal to provide the required analytical information on said species.

22 Claims, 5 Drawing Sheets

METHOD FOR OPTICALLY ASCERTAINING PARAMETERS OF SPECIES IN A LIQUID ANALYTE

The present invention concerns a method for ascertaining parameters in a liquid analyte, e.g. for determining species dissolved therein.

This method relates to the known techniques in which an optical waveguide carrying a totally reflected light signal is contacted with an analyte and the evanescent wave component of said signal interacts with the analyte at the solid-liquid interface in a manner responsive to some parameters inherent to the species therein. For instance, information on such parameters may concern an absorption of part of the luminous energy of the incident signal at the points of reflection thereof within the waveguide by the molecules of the species of interest at said interface or to an excitation of some fluorophores by said luminous energy with the consecutive production of a fluorescence signal characteristic of such species. In general, the interaction is limited to the region corresponding to the depth of penetration into the analyte of the evanescent wave component of the incident light, this depth ranging from a few tens to some hundred of nanometers starting from the waveguide surface.

Although it is generally known that the aforementioned interaction may provide information on some parameters in the bulk solution (Hardy, U.S. Pat. No. 4,050,895), recently published work has shown that improved results (i.e. better sensitivity and accuracy) are obtained when the effective interaction of the evanescent wave component with the analyte (or rather, the leaking into the analyte of a substantial portion of the energy thereof) is limited to involve a single layer (generally monomolecular) of compounds of interest bound to the surface of the waveguide. In other words, one has recently found that a very useful new analytical technique can be based on attaching to the waveguide, before contacting it with the analyte to be investigated, a reactant specific to a species of said analyte and, thereafter, immersing it into said analyte; under these conditions, the species of interest will bind to the said reactant and provide at the surface of the waveguide a layer of a complex whose concentration of the species of interest (i.e. the actual density of said species in the area of interaction) will grow very rapidly with time and provide increased interaction with the light travelling in the waveguide and stronger response at the output thereof (KRONICK and LITTLE, U.S. Pat. No. 3,939,350).

In such types of analysis involving the formation of a very thin layer of product of interest on the waveguide surface, the interaction of the light signal with the bulk of the solution is considered a nuisance (background noise) and attemps have been made to minimize it as much as possible. For instance, compromising condition between maximal interaction of the evanescent component with the monomolecular layer deposited on the waveguide surface and minimal interaction with the bulk solution can be achieved by controlling the depth of penetration of said evanescent component outside the material of the waveguide at the waveguide/analyte interface. Such control can be effected by selecting a waveguide with a suitable refractive index $n_1$ relative to that ($n_2$) of the solution and by choosing adequately the angle of total reflection in the guide as well as the wavelength of the incident light (more detailed explanation on why this can be so and how to make such selections will be provided hereafter). For instance in co-pending application EP-A-75353, it has been disclosed that this depth of penetration can be optimized to match with the thickness of said layer of interest or to be in excess thereof.

However, it has now been found that unexpectedly this approach is not always the most desirable; indeed, it has been found with surprise that, under some conditions, the penetration of the evanescent wave component distinctively beyond the distance corresponding to the thickness of the layer of interest can be extremely useful in concurrently providing analytical results on parameters of the analyte other than that specifically involved in said layer of interest, e.g. on species in solution in the analyte. Therefore, this discovery led to the definition of one aspect of a new analytical method. Moreover, this method was also extended to further aspects after realizing that useful interactions of the light carried by the waveguide with the analyte may involve more than one specific area of the waveguide (i.e. the area where interaction takes place with either a single layer coating on this area or with the bulk solution or, simultaneously with both bulk and coating), i.e. may involve two or several distinctly different areas of said waveguide. For instance, in one area the interaction will take place with the bulk solution and in another or more optically separated areas the interaction will take place with one or several layers of interest.

In the method of the invention, any type of interaction of the light guided in the waveguide with the analyte can be considered. Thus, this interaction can result from absorption of part of the signal, the output response being then a decrease in output energy gathered by collecting and detecting means located at the outlet of the waveguide. Alternatively, the interaction may result in the production of fluorescence if the species of interest (whether located in the bulk analyte or in a coating of interest at the waveguide surface) can generate fluorescence under excitation by the incident signal. Such is the case for instance in fluorescence type assays where one of the partners in a complex under formation on the surface of the waveguide comprises a fluorophore group which induces fluorescence upon formation of said complex. Otherwise, useful responses can also result from the scattering of the incident light by larger molecular aggregates built on the surface of the illuminated waveguide.

In order to practically carry out the method of the invention, one can for instance use a waveguide in the form of an optical fiber or a glass or plastic slide coated with a reagent specific to one first species dissolved in an analyte which additionally contains another or more species of interest. In an example to be developed in detail hereinafter, this first species can be a specific hemoglobin compound in a sample of blood also containing other hemoglobin or blood factors. Thus, in this case, the waveguide will carry, attached thereto, an antibody specific to that first species and, upon contacting the illuminated waveguide with the blood sample and arranging the measurement conditions (as specified hereafter) for providing an effective and signal generating interaction of the light in the waveguide with, simultaneously, the bulk solution and a monomolecular layer of a complex involving the antibody and that first species that forms on the waveguide surface, a signal is provided at the outlet of the guide, this signal being representative concurrently or simultaneously of the total hemoglobin (or other blood factors) having interacted in bulk with the excitation signal and of said first species involved in the formation of the complex.

In this case, the signal at the outlet of the waveguide is representative of two independent effects and can be decoded by simple means since the response to the bulk hemoglobin corresponds to an instantaneous partial extinction of the signal output collected from the waveguide end (this is actually the aforementioned background noise) while the response to the thin layer is a time dependent signal due to the formation of said complex layer of antibody and the first specific species to be determined which is a rate reaction.

Otherwise, if two specific factors in the analyte (for instance factor 1 and factor 2 among others present) must be determined, a waveguide with two independently working optical areas are preferably selected, each area being provided with one reagent (antibody) specific to one of said factors to be determined. In such case, the two response signals collected at the output of the waveguide (this being so if the waveguide is not provided already with separate outputs) are either (a) phase dependent or (b) frequency dependent.

Case (a) may be illustrated by a waveguide provided with two independent optical elements such as the two oppositely facing parallel walls of an analytical cuvette, said walls being light conductive for a fully reflected signal and each internally coated with one of the two aforementioned reactants, each being specific to one of the two factors (factor 1 and factor 2) to be determined in the analyte. In this case the two elements are illuminated in turn (alternately applied pulses), the mode of application being also used for synchronization purposes at the detecting and processing end to ensure proper separation and independent display of the corresponding signals.

Case (b) may be illustrated by a waveguide structure comprising two physically separated areas on the same light path of the waveguide (i.e. not separated optically) but providing responses at two different wavelengths or absorption at 2 different wavelengths in a simple cuvette (this can be implemented, for instance, by having one area responsive to absorption, e.g. at the absorption wavelength and another area providing a fluorescent response, i.e. a signal of an exitation wavelength different from the absorption wavelength). In this case the detector unit is provided with means to separate the components of the output consisting of a signal with two wavelengths into individual signals by usual means (band-pass filters or dichroic beam splitters). Such a situation can result for instance from attaching to a first area of the waveguide a first reagent specific of factor No. 1 to be analyzed, the layer of reaction product being light absorbing, and attaching to a second area of the waveguide a second reagent specific of factor No. 2, the reaction product of said second reagent and factor No. 2 being fluorescent under excitation by the incident light.

Of course case (b) can also be illustrated by a variant of the structure of case (a), i.e. with one of the separately illuminated waveguide element being responsive to absorption while the other is fluorescence responsive.

The practical aspect of the invention will now be illustrated with reference to actual analysis cases. The first case refers to blood analysis and, more particularly, to the direct determination in blood samples of hemoglobin and various other hemoglobin factors such as glycosylated hemoglobin, this being, if desired, relative to total hemoglobin in this sample.

Glycosylated hemoglobins ($HbA_{1a}$, $A_{1b}$ and $A_{1c}$) are important factors in the diagnosis and monitoring of patients with diabetes. The determination of the content of $HbA_{1c}$ (which amounts to about 80% of total glycosylated hemoglobins ($HbA_1$)) relative to total hemoglobin (i.e. $HbA_o$, non-glycosylated hemoglobin plus ($HbA_1$)) is particularly important with regard to that disease.

Hemoglobin $A_{1c}$ is a glycohemoglobin with an amino acid structure which is identical to that of $HbA_o$; the important difference is the presence of 1-amino-1-deoxy-fructose attached in the 2,3-diphosphoglycerate pocket to the N-terminal valine in the beta-chain of $HbA_{1c}$. The modification of $HbA_o$ to $HbA_{1c}$ is a continuous non-enzymatic post-translational process, the rate of which is a function of the blood glucose concentration. Glycosylation occurs as a two step process. Firstly, the open aldehydic form of glucose reacts with the terminal amino group of the beta-chains of Hb to form a SCHIFF base. Secondly, the SCHIFF base then undergoes an AMADORI rearrangement to form $HbA_{1c}$. The intermediate SCHIFF base is unstable with a 60-fold greater tendency to dissociate (to the free sugar plus protein) than the stable ketoamine of $HbA_{1c}$. As only a small fraction of blood glucose is in the open aldehydic form (approximately 0.001%) and the rate of ketoamine formation is slow (although effectively irreversible), the formation of $HbA_{1c}$ is an indication of long term blood glucose concentration. Over the 120 days life-span of the human red blood cell, the number of glycosylated Hb molecules increases proportionally to the mean blood glucose concentration. The relationship between the mean plasma glucose and $HbA_{1c}$ concentrations is unique in that a single $HbA_{1c}$ measurement provides a retrospective assessment of blood glucose control over the preceeding 6 to 8 weeks. It is generally accepted that $HbA_{1c}$ measurements are a very useful tool in monitoring diseases of carbohydrate metabolism, specifically diabetes mellitus. Diabetics have high long-term blood sugar levels and this is reflected in their $HbA_{1c}$ levels. Normal adults have about 3-6% of their total hemoglobin as $HbA_{1c}$ whereas the range in juvenile and maturity onset diabetics is 6-15% as $HbA_{1c}$. A similar increase in $HbA_{1c}$ concentration has been noted in mice with genetic and chemically induced diabetes and in pancreatectomized dogs.

Among the several methods which exist for determining glycosylated Hb in blood, $HbA_1$ and in particular $HbA_{1c}$ measurements have now become a method of choice for monitoring the treatment of diabetics (L. JOVANOVIC et al., American J. of Medicine (1981) 70, 331; D. E. GOLDSTEIN et al., Diabetes (1982) 31, 70; K. H. GABBOY et al., J. of Clinical Endocrinology and Metabolism (1977) 44, 859; B. GONEN et al., Diabetologia (1978) 15, 1; C. M. PETERSON, Diabetes (1982) 31, 1). Also, the following patent documents can be usefully mentioned: U.S. Pat. No. 4,247,553; GB-A-1,580,318; U.S. Pat. No. 4,222,836; U.S. Pat. Nos. 4,372,747; 4,200,435; 4,341,635. These methods can be readily classified by the mechanism used to separate glycosylated Hb from non-glycosylated Hb. For instance ion-exchange chromatography was used early and is still the most common method (H. G. KUNKEL et al., Science (1955) 122, 288). Although such ion-exchange technique is currently the only available method which specifically measures $HbA_{1c}$, it has a number of limitations of which temperature and pH sensitivity are the most important. Ion-exchange also is subject to interferences as labile glycosylated Hb (pre- $HbA_{1c}$) must be removed prior to assay and both fetal Hb (HbF) and Sickle Cell Hb (HbS) interfere with the results.

Other techniques involve agar gel electrophoresis (L. MENARD et al., Clinical Chemistry (1980) 26, 1598), isolectric focusing (K. M. SPICER et al., Diabetes (1978) 27, 384), colorimetry, e.g. with thiobarbituric acid (R. Fluckiger et al., FEBS Letters (1976) 71, 356) and affinity chromatography (V. BOURIOTIS et al., Diabetologia (1981) 21, 579). Only one type radioimmunoassay has been reported (J. JAVID et al., British J. of Haematology (1978) 38, 329) which was slow (more than 3 days to work) and technically complex as requiring the preparations of radiolabelled $HbA_{1c}$. Although the methods of the prior art have merits, there is still a need for methods providing quick results (less than about 15 minutes), requiring less skilled operators and less costly to be undertaken on a routine basis. Current art methods are slow (typically more than 1 hour for results), technically complicated (require more than five pipetting manipulation steps) and unsuited to testing outside a laboratory environment. Further, present methods require that total hemoglobin be ascertained separately from the glycosylated factors and it would be desirble that both analytical data can be ascertained substantially together and correlated without delay.

The method of the present invention thus, remedies the inconvenience of prior art methods and further offers the advantage of directly relating, if desired, the percent of glycosylated factor or other hemoglobin factors to total hemoglobin.

The present method allows for the separate determination of (Hb) $A_{1c}$, $A_{1a}$ or $A_{1b}$ provided antibodies specific to any of such species are available in purified form. Otherwise, using less specific antibodies, the present method allows for the combined determination of two or more blood factors taken together, i.e. all glycosylated Hb relative to total Hb for instance. Of course, the method also provides for the determination of blood factors other than the ones hereabove if corresponding reagents specific to said factors in complex formation reactions are available (e.g. HbF, HbS or other human hemoglobin variants.

The present invention does not concern the obtention or preparation of such specifically reactive complex moieties (monoclonal or polyclonal antibodies) which belong to the prior art but it concerns their use as coating materials in the preparation of the active wave guides to be contacted with the blood sample to be analyzed according to the invention.

The waveguides used in the present methods can be of many kinds and some have been disclosed in copending application EP-A-75353 together with the methods for coating the wave guides with the reactive antibodies selected.

In the present case, plate-like or fiber optic waveguides included as members of an analytical cuvette are preferably used, the coated surface of the waveguides being put into contact with the blood sample once the latter has been injected into the cuvette.

The optical technique used here relates, as discussed hereinabove, mainly to light absorption, i.e. there is an interaction of the evanescent component of the wave transported in the guide with the molecules, first in the ambient liquid (the depth of penetration the evanescent component exceeds somewhat the thickness of the antibody coating, which provides an instantaneous response) and, second, with the Hb-antibody complex which starts building up on the guide in forms of an additional layer due to the reaction of the blood factor to be determined with the specific complex moiety (antibody) previously coated on the guide surface. Although the depth of interaction of the evanescent light component is not substantially limited to the thickness of the layer of the complex, it has been surprisingly found that optical response to that build-up is independent of the bulk absorption due to the blood itself and the two effects can be easily distinguished without sophisticated techniques for decoding the signals originating from one or the other effect.

Hb derivatives have characteristic absorption spectra dependent on their chemical state. Hence, any of the usual absorptiometric techniques are equally applicable for implementing the invention (L. TENTORI et al., Hemoglobin, in Methods in Enzymology (1981), vol. 76, 707-732, Academic Press, New York). Included are the cyanomethhemoglobin method and single or multi-wavelength absorptionmetric assays, preferably in the range 400 to 600 nm, specifically 400-420 nm and 550-600 nm. Also included are such isobestic point methods where the absorption by the Hb molecule is independent of the degree of oxygen saturation.

BRIEF DESCRIPTION OF THE DRAWINGS

The invention and its present illustrative aspect will be better understood with help of the accompanying drawings.

FIG. 4b is a schematic view of a variant of the embodiment of FIG. 4a.

Figure 1A:
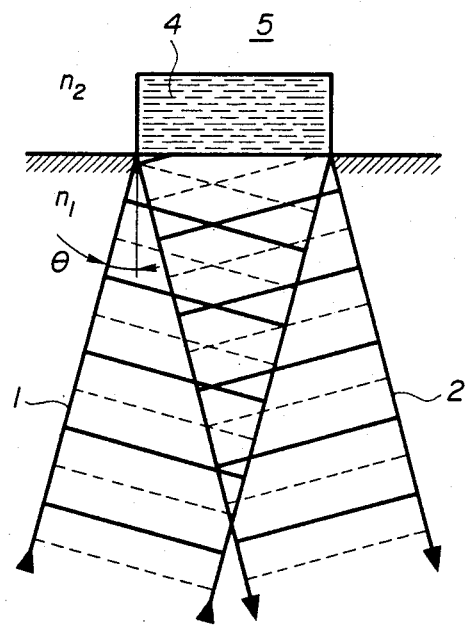
FIG. 1a is a diagram explaining the propagation of totally reflected light in a medium (wave guide) of refractive index $n_1$ greater than $n_2$, the refractive index of another medium (analyte) with which the wave guide is in contact.

As said before, when a light beam 1 strikes with an angle $\theta$ the interface between two transparent media $n_1$ and $n_2$ (FIG. 1a), striking from the medium $n_1$ with the greater refractive index ($n_1 > n_2$), total internal reflection occurs (N. J. HARRICK, Internal Reflexion Spectroscopy, Wiley Interscience, New York (1967)) when the angle of reflection $\theta$ is larger than a certain value $\theta_c$ called the critical angle given by the equation:

$$\theta_c = \sin^{-1}(n_2/n_1) \qquad 1$$

Figure 1B:
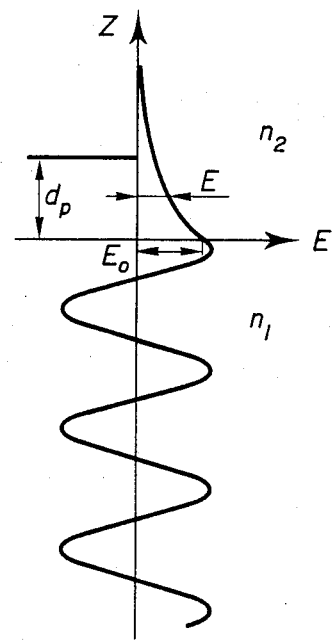
FIG. 1b is appendent to FIG. 1a and schematically represents the penetration of the evanescent wave component in the rarer medium (analyte).

The reflected beam is indicated by numeral 2. In this case the evanescent wave penetrates a distance ($d_p$) of the order of a fraction of a wavelength beyond the reflecting surface into the rarer medium of refractive index $n_2$. According to Maxwell's equations a standing sinusoidal wave, perpendicular to the reflecting surface, is established in the denser medium (FIG. 1b). Although there is no net energy flow into a non-absorbing, rarer medium, there is an evanescent, nonpropagating field 3 in that medium, the electric field amplitude (E) of which is largest at the surface interface (Eo) and decays exponentially with distance (Z) from the surface according to:

$$E = E_o \cdot \exp(-Z/d_p) \qquad 2$$

The depth of penetration ($d_p$), defined as the distance required for the electric field amplitude to fall to exp($-1$) of its value at the surface, is given by:

$$d_p = \frac{\lambda/n_1}{2\pi(\sin^2\theta - (n_2/n_1)^2)^{\frac{1}{2}}} \qquad 3$$

Starting from 90°, as $\theta$ approaches $\theta_c$, $d_p$ infinitely large, and at a fixed angle, increases with closer index matching (i.e., as $n_2/n_1 \to 1$). Also, because $d_p$ is proportional to wavelength, it is greater at longer wavelengths.

Thus, by an appropriate choice of the refractive index $n_1$ of the transparent wave guide, of the incident angle, and of the wavelength, one can select a $d_p$ to control optical interaction, either mainly with substances 4 close or at given distance from the interface and minimally with substances 5 beyond said distance or, with varying response ratios, with both 4 and 5. And this is precisely one of the key factors of the present invention, i.e. to have established that appropriate selection of said parameters ($n_1$, $\theta$ and $\lambda$) provides optimal conditions for measuring, at the same time, two independent parameters in the analyte. In the present embodiment, the denser medium can be constituted by a quartz microscope slide ($n_1 = 1.54$) and the rarer medium is aqueous blood sample ($n_2 \approx 1.34$) and $\theta$ is controllably variable so that when $\lambda$ is a selected visible wavelength, $d_p$ can be varied from about 20 to 300 nm until optimal response is provided. Of course, other materials for the waveguide can be used with refractive indices other than 1.54.

Although single reflection systems can be used, one can enhance sensitivity (lower the limit of detection) by combining the evanescent wave principle with multiple internal reflections. The number of reflections (N) is a function of the length (L) and thickness (T) of wave guide and angle of incidence ($\theta$):

$$N = L/T \cdot \cot\theta \qquad 4$$

The microscope slide waveguides used in some of the experiments had an active length of 36 mm, thickness of 1 mm and the angle of incidence varied from about 60° to 75°. Thus the number of reflections on one side for a discrete light beam was approximately 6. Similarly, in another embodiment using a fibre optic waveguide, the latter had an active length of 64 mm, a thickness of 0.6 mm and, with the same angles of incidence the total number of reflections for a discrete light beam varied from about 30 to 40.

As said before, the method of the invention can also rely on fluorescence effects. Fluorescence emission generated at a waveguide liquid interface can also be monitored at the waveguide output. As predicted by the theory of reciprocity and demonstrated with dye molecules in both monomolecular layers (CARNAGLIA and MANDEL, J. Optical Soc. of America 63, 479 (1972)) and in monodispersed spheres (LEE et al, Applied Optics 18, 862 (1979)), fluorescence emission at a waveguide/liquid interface can be treated as an evanscent wave. In effect, excitation of fluorescence by an evanescent wave produces fluorescence emission with the characteristics of an evanescent wave and thus generates an internally reflected beam of fluorescent light. The direction of fluorescence emission of this form is mainly a function of the respective refractive index ratio and has the major characteristic (see the above Carnaglia reference) that photon emission has a distribution of "preferred" angular probability close to the critical angle ($\theta_c$).

In practical terms this means that fluorescence can be monitored at the output of the waveguide in the same optical plane as the excitation light. Theoretically, this has the advantages of concentrating the fluorescent emission intensity within a small angle; also, these fluorescent photons do not pass through the bulk of the solution and thus are not subject to major optical interference (e.g. absorption, scattering).

This technique is disclosed in more detail in co-pending application EP-A-75353.

For the fluorescence measurements illustrating the present invention, the excitation wavelength was selected at 490 nm and fluorescence emission measured (wavelength greater than 510 nm) at the waveguide output by positioning cut-off filters before the photodetector element (KV 8.5; 50% transmittance at 320 nm; SCHOTT GLASS WORKS, Mainz, Germany).

Fluorescence techniques allowing for the simultaneous determination of two or more parameters, for instance with multi-analyte waveguide systems have many applications in the field of clinical diagnostics, e.g. simultaneous measurement of the thyroid hormones $T_4$ and $T_3$, the gonadotrophins LH and FSH, tumor markers such as AFP and CEA; also the whole gamut of cell surface antigen determination as applied to clinical microbiology.

Figure 2:
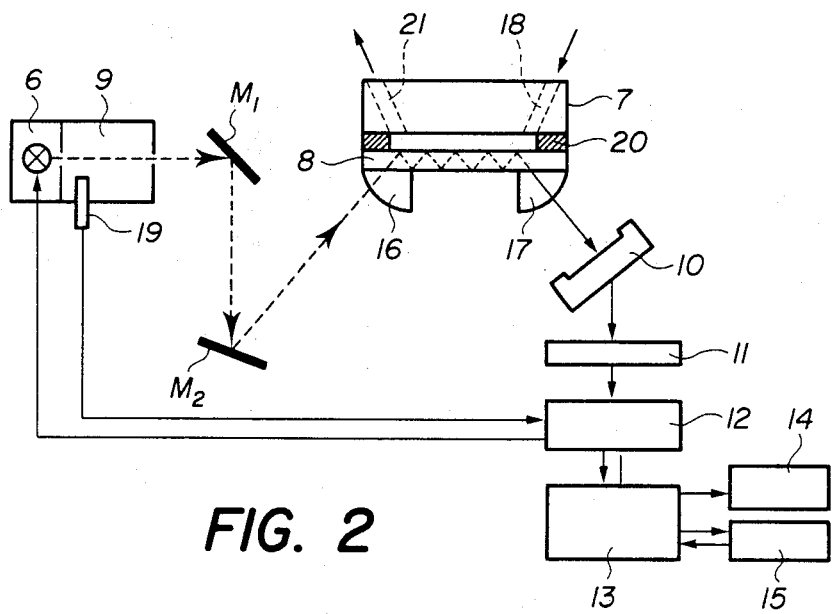
FIG. 2 is a schematic layout of a single waveguide apparatus for carrying out the method of the invention.

One embodiment of the apparatus used is schematically represented on FIG. 2 which shows as a block diagram the major components; these components comprise a monochromator 9, a light source 6, a flow cell 7 with waveguide 8, and electronics with data-acquisition and processing microcomputer including a photomultiplier detector 10, a preamplifier 11, a microprocessor light source control system 12, a microcomputer 13, a printer 14, and a memory (floppy disc) 15.

The light source 6 in this instance was a xenon flash lamp (E.G. & G., Salem, MA) and the monochromator was equipped with a concave holographic grating (Jobin-Yvon, Paris, France) to permit a resolution of 5 nm. The flash lamp operation was controlled by microcomputer 12. To inject the samples through an input 18 to the cell 7 a programmable automatic pipette (Microlab- P; Hamilton Bonaduz AG, Bonaduz, Switzerland) was preferably used. The optical component further included two mirrors $M_1$ and $M_2$ and two prisms 16 and 17. A photomultiplier tube of the detector 10 (R928; Hamamatsu, Tokyo, Japan) placed at the waveguide output monitored the change in light intensity directly. Signals from the photomultiplier tube were amplified (11), integrated during the flash time (12) and converted by a standard 12-bit analog/digital converter (not shown) into digital format. The in-house developed microcomputer 12 performed fast signal averaging, and all data were adjusted for variation in flash lamp intensity by reference to a photodiode 19 placed in the monochromator. The signals were transmitted to a microcomputer 13, preferably an APPLE II model, for display and storage. Two different embodiments of waveguide systems were used:

The analytical cell or cuvette illustrated on FIG. 2 as one embodiment, is based on a microscope slide waveguide system. The illustrated system shows the flow cell 7 whose bottom is actually the microscope slide 8. Tightness is ensured by a gasket 20; the slides 8 were placed in direct optical contact by use of index matching oil with two quarter-round silica prisms 16 and 17, preferably from Heraeus. The index matching oil, thereby removed the requirement for specially polished, optically flat waveguide faces. The prisms were designed to allow easy adjustment of the angle of incident light $\theta$ (see FIG. 1a) and to avoid contact of light with the sealing gasket 20.

The flow cell, machined from aluminum alloy, met the criterion of allowing rapid, bubble-free laminar flow along the light path. Its design also ensured rapid and accurate demounting and repositioning. We chose an aluminium alloy, although other metals are also suitable, e.g. brass, because of its good thermal conductivity, relative lack of reactivity with saline solution, and low optical reflectivity after being anodized matt black to avoid stray light effects. The gasket 20 was 0.5 mm thick medical grade silicone rubber and water tight under a constant sealing pressure of 2 kg/cm$^2$. Including input 18 and exit 21 ports the total cell volume was 1.8 ml, the volume directly above the waveguide was 0.66 ml (53×25×0.5 mm) and the volume above the light path was 0.29 ml (36×16×0.5 mm).

Figure 3:
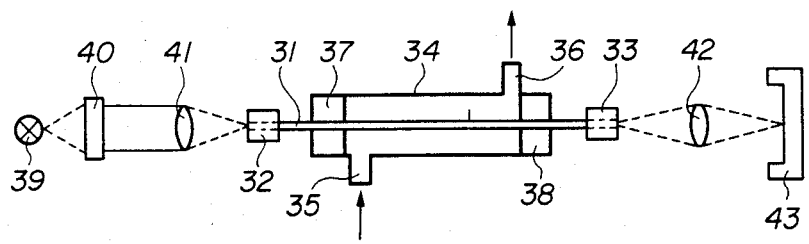
FIG. 3 is a schematic layout of another embodiment of an apparatus for carrying out the method of the invention.

A second embodiment (see FIG. 3) is based on a fibre optic system. The fibre waveguide 31 was prepared from standard transmission optical fibres by first cutting them into 120 mm pieces, then removing the silicone cladding with tetrafluoroethylene to expose an optically active surface area of 120 mm$^2$. The ends of the fibres were polished and held within specially made stainless steel end-fittings 32 and 33 (7×3 mm internal diameter) for support and protection. The fibre flow cell 34 was an open-ended quartz tube (internal diameter 4 mm, length 80 mm) with input 35 and output 36 tubes added for inserting and removing sample. The fibres were set in place in the flow cell with silicone rubber plugs 37, 38. Light from source 39 was focussed and filtered (40, 41) with a lens onto the end of the fibre at a mean aperture angle of 68° (see FIG. 1); at the fibre output, light was refocussed by means of a lens 42 onto a photomultiplier tube 43.

Figure 4A:
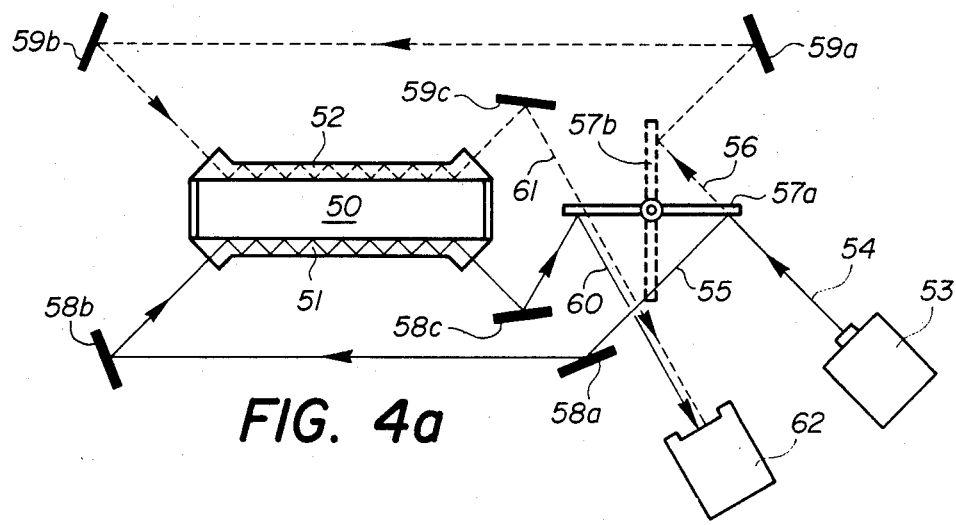
FIG. 4a is a schematic top view of a detail of another embodiment of an analytical apparatus involving a double waveguide cell.

The apparatus of which the essential optical components are schematized on FIG. 4a comprises a dual-waveguide cell 50 of which the main walls 51 and 52 constitute two independently energized elements that transport the exciting signal originating from a source 53 and whose inner walls, either bared, blocked or coated with a specific reactant, are in contact with the analyte solution contained in cell 50. The especially shaped light conductive walls of the cuvette can be provided by usual means, e.g. by molding with a transparent plastic, for instance lucite. These walls can be made from materials with the same or different refractive indices.

The beam of light 54 originating from source 53 is alternatively split into beams 55 and 56 by a rotating chopper mirror 57a, b. On FIG. 4a, this mirror 57 has been represented in two positions, i.e. one position corresponds to numeral 57a and another position (at about right angle to the first one) by numeral 57b. It can be readily seen that, depending on the position of the mirror 57, the beam 54 is either reflected into beam 55 or propagated into beam 56. Thus, the light from the source 53 is alternatively injected in either portion 51 and 52 of the dual waveguide cell 50 by means of either one of a series of mirror 58a, b, c and 59a, b and c, respectively. The output light, respectively 60 and 61, from either part of the waveguide is then collected on a detector 62.

The remaining components of this embodiment are not represented on the drawing as being known from the art and identical to the corresponding elements disclosed in connection with the embodiment of FIG. 2.

In a further embodiment, (see FIG. 4b), the apparatus comprises a dual-waveguide cell 70 identical with the cell of the previous embodiment, i.e. having walls 71 and 72 acting as the two independent elements of the waveguide and operating similarly as will be seen.

The apparatus comprises a light source 73, the output of which is focussed on either side by means of lenses and mirrors, (the mirrors are indicated by numerals 74 and 75) on the input side of guide elements 71 and 72, respectively. A chopper disk 76 with a window hole 77 acts to alternately distribute the exciting light into elements 71 and 72. The output signals from the waveguide are then directed to a detector 78 by means of mirrors 79 and 80.

Figure 4B:
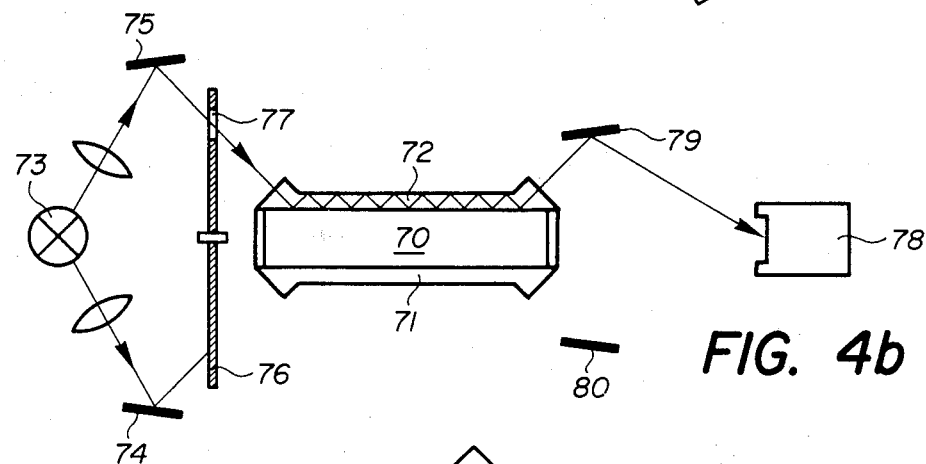

In both embodiments depicted on FIGS. 4a and 4b, one of the waveguide elements (51, 71) is coated with an antibody specific to one component to be measured in the analyte by a complexation reaction (as disclosed hereintofore) while the second element (52, 72) is left uncoated. Herein, uncoated refers to a surface without antibody. However the protein adsorption sites on this surface are usually blocked by adsorbing a protein (e.g. BSA) to the surface. Therefore during analysis, the signal collected at the output of the uncoated area reflects the interaction of the exciting beam with the bulk of the analyte, i.e. it provides the desired information on the total hemoglobin in the sample. However, simultaneously, the signal emerging from the coated side of the guide provides the required information on the component being bound by the specific reactant coated on the inner surface of this side of the cell. This will be illustrated in more detail with reference to Example 4 in this application. Suffice to say now that this kind of waveguide system (dual type) allows to gather the two types of information from separate areas of the waveguide (i.e. the phenomena are no longer superimposed like in the earlier embodiment) which may provide more accuracy in the determinations.

Figure 4C:
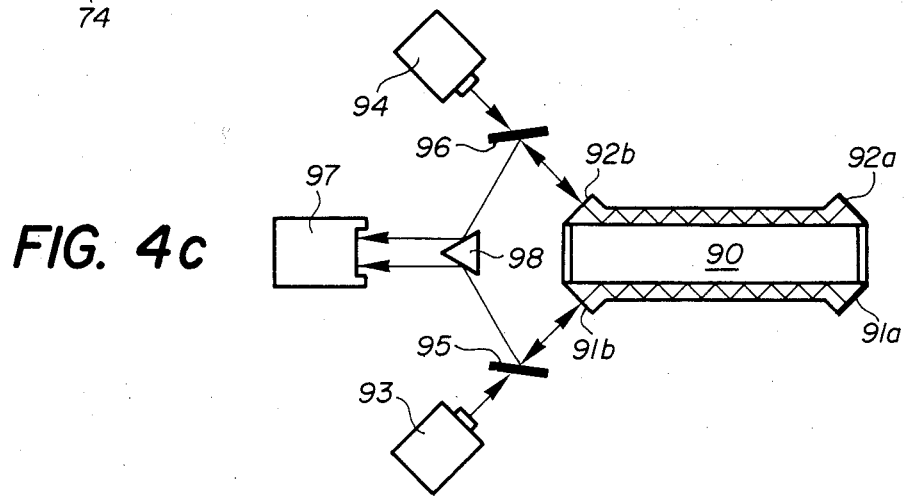
FIG. 4c is a schematic view of still another embodiment.

A variant embodiment is represented on FIG. 4c. In this variant, a dual waveguide cell 90 of the same general configuration as the aforementioned cells 50 and 70 is used with the difference that ends 91a and 92a are actually made reflective, for instance by metallizing (silver) like with a mirror. Therefore, the other ends 91b and 92b, respectively, of the waveguide light conductive elements act simultaneously as input and output ends. This is illustrated by the paths of the exciting light beams provided by two sources 93 and 94 which are directed into ends 91b and 92b, respectively, after crossing beam-splitters 95 and 96, respectively. Thus, the light which penetrates through ends 91b and 92b travels through the guide first in a forward direction and then backwards after being reflected from ends 91a and 92a. This configuration enables that the interaction capacity of the exciting light with the analytes be actually doubled as compared with the previously disclosed embodiment. This variant further comprises a detector 97 for collecting the backward signals exiting from 91b and 92b and directed thereto by meams of beam splitters 95 and 96 and a triangular shaped mirror 98. Sources 93 and 94 are alternatingly synchronized so that signal pulses exiting from the waveguide ends 91b and 92b do not simultaneously fall on the detector 97.

Figure 5:
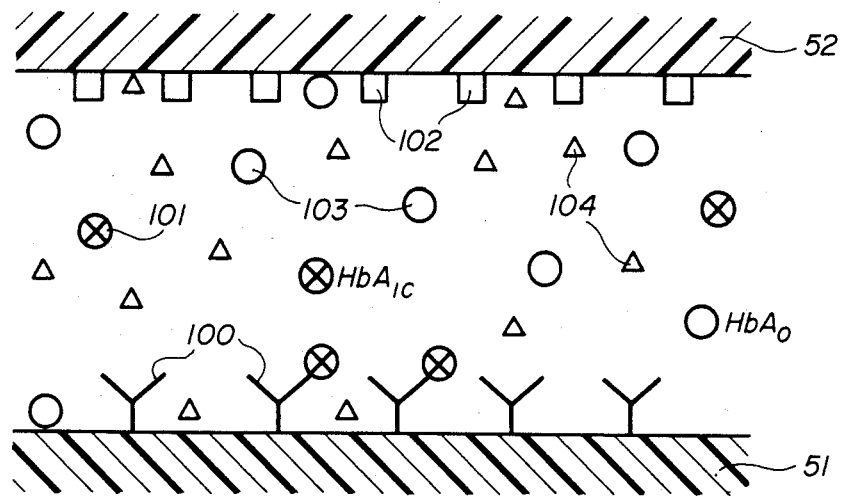
FIG. 5 is a schematized representation of the phenomena occurring during an analysis according to the method of the invention.

FIG. 5 is a schematic illustration at the molecular level of the phenomena taking place during analysis in a cell of the dual-waveguide type as disclosed previously. In FIG. 5 areas marked 51 and 52 correspond for instance to the waveguide elements 51 and 52 depicted on FIG. 4a. The area intermediate between areas 51 and 52 represents schematically an analyte medium with species dissolved therein and reactants or species attached to the inside walls of elements 51 and 52. Element 51 is pictured to have deposited thereon antibodies 100 specific to $HbA_{1c}$ entities labelled 101. Some of these $HbA_{1c}$ molecules are shown after complexation with the specific antibody 100, others are still free. The other surface (i.e. the surface of element 52) is shown coated with blocking agents 102 (for instance, bovine serum albumin) said agents being intended to minimize the possible affinity of the bare wall to other species in solution, for instance $HbA_o$ 103 and other proteins of any type 104.

Thus, during analysis, non specific binding of Hb to surface 52 is prevented (or at least strongly minimized) which makes it possible to measure the bulk hemoglobin by the interaction of the evanescent wave component of the signal travelling in 52 with the analyte solution at depths beyond that of the blocking coating deposited on the surface.

In contrast, a complexation reaction occurs on surface 51 between the antibody molecules 100 coated thereon and the $HbA_{1c}$ (AG) molecules in the analyte solution. This reaction although rapid is not instantaneous; therefore a layer of complex progressively builds up on surface 51 with consecutive corresponding interaction with the light component travelling in that element of the waveguide, this resulting in the production of response curves of the A or B type depicted in FIG. 6 (see the Examples that follow).

In order to practically carry out the tests, the microscope slides were cleaned by consecutive immersion in concentrated sulfuric acid and distilled water, ethanol, and acetone, using standard slidestaining glassware. Fibres were cleaned in ethanol ultrasonically and, supported on glass rods, were immersed in the various antibody solutions. Antibodies were either physically adsorbed to the surface of the waveguides or covalently coupled. Adsorption was carried out by incubating cleaned waveguides with solutions of antibody (5 mg of protein/ml of 0.05 ml/l Tris Hcc buffer, pH 7.0) for four hours. Unadsorbed proteins were washed away with saline and residual protein binding sites blocked by incubation of the antibody-coated waveguides with bovine serum albumin (1.0% by weight in TRIS Buffer). The method of coupling was essentially that of Weetall, involving aminopropyltriethoxysilane APTS (Immobilized Biochemicals and Affinity Chromatography, R. B. Dunlop, Plenum Press, New York, p. 191–212) in an acid aqueous silanization environment. (Immobilized Enzymes, Antigens, Antibodies and Peptides: Preparation and Chromatography, 1: Enzymology, H. A. Weetall, Marcel Dekker Inc. New York 1975, p. 1–48).

In general, we reacted waveguides with APTS (0.4 mol/l) for 3 hours at 80° C. We then heated the slides or the cuvette walls at 120° C. and the fibres at 100° C. for 2 hours, then let them soak in glutaraldehyde solution (0.5 mol/l) in phosphate buffer (0.1 mol/l, pH 6.8) for 90 min at ambient temperature. The "activated" waveguides were then reacted with antiserum Ab (5 mg of protein per milliliter of phosphate buffer) for 24 hours at 4° C. After washing the antibody-coupled waveguides in phosphate buffer, we stored them at 4° C. in isotonic saline (0.14 mol/l, containing sodium azide, 8 mmol/L). Measurements of protein (Anal. Biochem 51, 654–655 (1973)) before and after the coupling demonstrated protein uptakes of approximately 1 $\mu g/cm^2$ of quartz.

The following Examples illustrate the invention in more detail.

EXAMPLE 1

(To demonstrate the existence of two distinct optical phenomena:
  (i) interaction of the evanescent wave component with hemoglobin in bulk,
  (ii) interaction of the evanescent wave component with the Ag/Ab complex under formation).

The apparatus used was that of embodiment of FIG. 2.

Preparation of standards with known solutions of hemoglobin.

Purified hemoglobin A (HbA) was obtained from SERVA FEINBIOCHEMICA, Heidelberg, FRG. Bovine Serum Albumin (BSA) was from SIGMA CHEMICAL CO., ST. Louis, MO, USA. All chemicals for buffers and solvents were Analar or Reagent Grade from MERCK, Darmstadt, FRG, or BDH, Poole, Dorset, UK. Rabbit antiserum to human HbA was purchased from DAKO, Copenhagen, Denmark.

Waveguides were fused-silica microscope slides (Suprasil 75.0 mm×25 mm×1 mm) from HERAEUS QUARZSCHMELZE GmbH, FRG.

Slides were cleaned by consecutive immersion (10 min each) in concentrated sulphuric acid, distilled water, ethanol and acetone. Antibody was coated to the surface by incubating the cleaned slides for 1 hour in a solution of anti-HbA diluted five-fold in phosphate buffered saline (PBS; 0.1 mol/L phosphate, pH 7.4, 0.9% (w/v) NaCl). Following rinsing with distilled water, remaining protein binding sites were blocked by incubation for 1 hour with 1% (w/v) BSA in PBS. Slides were then rinsed in distilled water and stored at 4° C. in isotonic saline prior to use.

Slides were fixed in conformity to the first embodiment illustrated on FIG. 2 in a manner which allowed light to be coupled into the slides at different angles $\theta$. The flow cell 7 was fixed to the surface via a 0.5 mm silastic gasket 20 and bubbles purged from the system by pumping assay buffer (PBS+5.0% (w/v) BSA) through the cell. Standard Hb solutions (1.0, 0.5, 0.1, 0.05 mg/ml) were made up in assay buffer to give a final protein concentration of 5 mg total protein/ml.

The assay procedure was initiated by injecting 3.5 ml of standard Hb solution into the cell after establishing a base-line signal. The wavelength of the input beam was selected by adjusting the monochromator at 410 nm and the reaction was monitored by the reduction in intensity at 410 nm. The angle $\theta$ was first selected at random above 66° (the critical angle). A value of about 67° was used in the test reported below.

Figure 6:
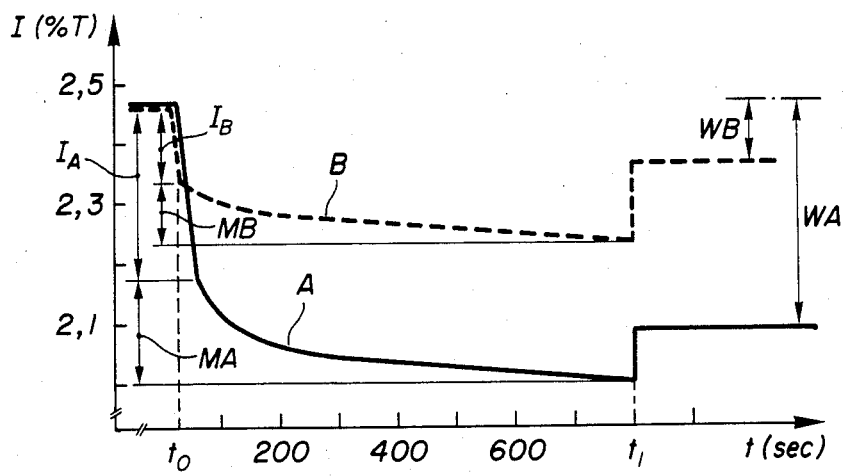
FIG. 6 is a diagram showing response curves in performing an analysis according to one embodiment of the invention.

Illustrated by FIG. 6 are the antibody-binding curves obtained with the 1.0 (curve A); and 0.1 mg/ml (curve B) Hb standards, using successive antibody-coated slides. After stabilising the base-line, the standards were injected at $t_o$ and an immediate fall ($I_A$, $I_B$) in transmission (arbitrary units) was followed by a slower but still rapid binding event which continued over the next 10 minutes. The initial fall was due to free hemoglobin molecules optically absorbing within the $D_P$ range of the evanescent wave (see FIG. 1). Note that at this early stage the complex layer is starting to form; therefore the evanescent wave component extends quite significantly beyond the initial Ab coating and is free to interact with the bulk solution. The subsequent slower change in signal of rate K and magnitude, respectively, $M_A$ and $M_B$ at time $t_1$ was due to antibody-binding of Hb at the surface. In the absence of antibody the signal changed minimally after the initial immediate fall. This was shown in a control experiment not shown on the drawing using no Ab coating.

Then the cell was washed with assay buffer ($t_1$) which removed all unbound materials. The residual absolute change in signal (WA, WB) is related to dose as indicated in the table below.

|  | Absolute change in signal | | |
| --- | --- | --- | --- |
|  | Test | Replicate | Mean |
|  | 1 | 2 |  |
| Dose Hb (mg/ml) |  |  |  |
| 0.1 | −4.6% | −4.3% | −4.3% |
| 1.0 | −14.9% | −12.5% | −13.7% |

The standard curves A and B were usable as templates for the determination of hemoglobin in unknown samples of blood. Similarly reproducible information could be gathered from measured values $M_A$ and $M_B$ provided unknown samples were measured after a constant time $t_1$.

EXAMPLE 2

Optimalization of the incident angle ($\theta$) vs sensitivity.

Figure 7:
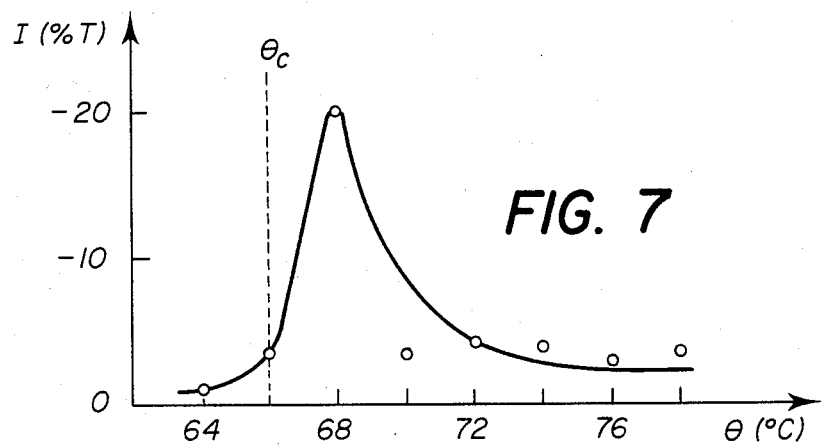
FIG. 7 is a diagram showing the variation of one parameter of the response curve as a function of the angle $\theta$ of incidence of the multiply reflected light beam travelling through the waveguide.

With an antibody-coated slide in place, Hb standard solution (1 mg/ml) was injected into the flow cell. After 10 minutes reaction the unbound materials were washed out of the cell with assay buffer. Bound materials were monitored by the reduction in transmission at 410 nm. The effect of incident angle of light was investigated by varying the angle ($\theta$) from 64° to 78°. The critical angle ($\theta_c$) is 66°. The results were plotted as the % transmission decrease (=sensitivity) vs angle of incidence (FIG. 7). It can be seen that with this system measurement of antibody-binding of Hb is possible with angles between 66° at 70°, with an optimum near to 68°. Larger angles have too small a penetration depth in this case although they may suit analytical systems of a different kind; smaller angles result in refraction not reflection. Angles between 66° and 68° are less suitable because the beam has a certain angular spread to that the light is only partially reflected and partially refracted, the latter part being lost from the system.

EXAMPLE 3

Preparation of more refined standard curves.

Hb standard solutions were incubated with separate antibody-coated slides and the reaction monitored using $\theta$=about 68° as the optimal angle. The results expressed as % transmission, show a dose-response relationship:

| Standard Hb (mg/ml) | % Transmission |
| --- | --- |
| 1.0 | 87.2 |
| 0.5 | 94.0 |
| 0.1 | 94.4 |
| 0.05 | 95.3 |
| 0 | 100 |

The minimum detection limit of this system is about 0.1 mg/ml or 0.1 g/l. Normal adult HbA values are 135–175 g/l, normal HbAlc levels are 4–9 g/l, thus this method can be used with ×10–×100 dilution of normal samples with adequate sensitivity.

EXAMPLE 4

Measurement of hemoglobin in the presence of foreign hemoglobin.

Solution samples were prepared based on avian hemoglobin (pigeon) and containing variable proportions of human hemoglobin to be measured. The total of both hemoglobins was always 5 mg/ml and the proportions of human hemoglobin are given in the Table below. A dual waveguide of the type shown in FIGS. 4a and 4b was used, one of the surfaces (e.g. 51) being coated with antibody to human Hb. The other surface (52) was blocked with bovine serum albumin as usual.

Upon doing the measurements a sharp drop (I) corresponding to 75.3% transmission was observed in all cases; then the further drop in transmission (M) (cf. with Example 1 and FIG. 6) was recorded after an interval of 10 min. In the case of the sample containing only avian hemoglobin, no further change during the 10 min interval was observed. The results are summarized below.

| Human Hb in avian Hb (%) | Transmission (%) (after 10 min) | M |
| --- | --- | --- |
| 0 | 75.3 | 0 |
| 1 | 74.9 | 0.4 |
| 2 | 74.4 | 0.9 |
| 10 | 72.0 | 3.3 |
| 20 | 68.3 | 7.0 |

Thus the value recorded for the first initial drop I can be correlated with the total hemoglobin present while the values (M) observed after the 10 min reaction period and corresponding to the binding of the human hemoglobin factor to the antibody coated on surface 51 can be correlated with the human hemoglobin content of the sample and its ratio to total hemoglobin. Standard curves were made from the above data by recording on an automatic recorder coupled to the apparatus used in this Example. Such curves were thereafter used as comparative data for determining unknown mixtures of human hemoglobin in avian hemoglobin.

EXAMPLE 5

Measurement of glycosylated Hemoglobin (HbA$_{1c}$) in the presence of hemoglobin.

Standard glycosylated Hb (HbA$_{1c}$) was prepared from pooled heparinized whole blood by cation-exchange chromatography (L.A. TRIVELLI et al., New England J. of Medicine 284 (1971), 353), using Bio-REX 70 resin (BIO-RAD, Richmond, Ca, USA). The purified HbA$_{1c}$ was then used to prepare standard samples by recombining it in varying known amounts with blood free from the glycosylated hemoglobin. The concentrations of HbA$_{1c}$ relative to total hemoglobin in the samples varied from 1 to 20% by weight and the total Hb concentration was of the order of 150 g/l.

Figure 8:
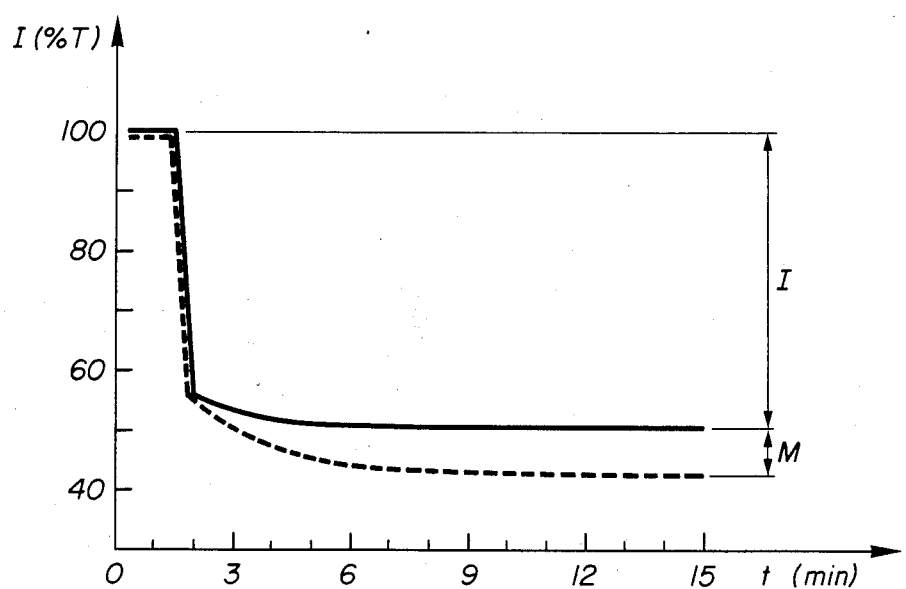
FIG. 8 is a diagram with a typical response curve in the analysis of $HbA_{1c}$ in the presence of hemoglobin.

An analytical apparatus with cuvettes involving a dual waveguide as illustrated on FIG. 4b was used for the determinations; the inner surface of one side of the cuvette was plated with antibody specific to HbA$_{1c}$ while the surface of the opposite side was left free. The content of each cell (a fresh one was used for successively testing each standard) was about 1 ml and 0.1 ml of the standard to be measured with about 0.9 ml of PBS were pipetted therein. FIG. 8 depicts one of the titration curves obtained after 15 min incubation time (with the 20% HbA$_{1c}$ sample), the upper curve (nearly flat) being that recorded with the uncoated part of the guide and the lower curve showing the response of the antibody coated part of the waveguide.

The results of the analysis of the various standards are also gatered in the table below.

| Standard sol. under test (% HbA$_{1c}$) | (%) Transmission in waveguide | | Difference M (%) |
|---|---|---|---|
| | uncoated side | coated side | |
| 0 | 56.1 | 55.8 | 0.3 |
| 1 | 55.5 | 54.7 | 0.8 |
| 5 | 55.7 | 50.2 | 5.5 |
| 10 | 58.0 | 49.2 | 8.8 |
| 20 | 54.9 | 42.4 | 12.5 |

The difference of 0.3% for the zero HbA$_{1c}$ sample may indicate some degree of residual affinity of the HbA$_{1c}$ specific antibody for the deglycosylated blood medium. This factor is however considered negligible under practical analytical conditions.

It should also be noted that the % transmission in the uncoated part of the waveguide was not constant from one cell to the other seeming to indicate that the method is not suitable for accurately determining total Hb. However it is not necessary in this instance to measure total Hb, but only to relate the signals from the uncoated and coated sides. Secondly, it is difficult to maintain a degree of constancy in manually fabricating a series of cuvettes such that each will enable full reproducibility of absolute measurements without initial calibration of the equipment. Undoubtedly, when cuvettes are manufactured industrially by molding on a large scale, this disadvantage is overcome.

EXAMPLE 6

The simultaneous determination of human IgG and human serum albumin (HSA) by fluorescence type assay.

The dual waveguide system as in the previous Example was used, a cut-off filter to block the incident radiation at 490 nm and pass the fluorescent signal at 520 nm being inserted on the light path before detector 78. The exciting light was generated by a monochromator of the type (9) disclosed in connection with FIG. 2.

One wall surface (A) of the cuvette serving as the dual-waveguide was coated with sheep raised antiserum against IgG. This was effected by adsorption according to usual means using a diluted solution of antiserum ($\sigma$-chain specific; SAPU, Carluke, Scotland; dilution by volume 1/400). The oppositely facing wall (B) of the cuvette was coated by the same technique with sheep antiserum against HSA (final dilution 1/100 by volume) obtained from the source.

Then, mixed combination standard solutions were prepared by dissolving together human IgG (SERVA BIOCHEMICALS) and HSA (UCB-BIO-PRODUCTS, Brussels, Belgium). Concentrations of reagents in the standards were 0.1; 1.0; 10.0 and 100.0 $\mu$g/ml. The solution buffer used as the standard medium was phosphate buffer 0.05 mole/l (pH 7.4); 0.9% NaCl (W/v); 0.05% NaN$_3$ (W/v); Tween 20 (SIGMA) 0.1% (v/v) and 2% (v/v) normal sheep serum (SAPU).

The test disclosed in this experiment was based on making a "sandwich" type assay i.e. the cuvettes were contacted with the standards and incubation was carried out for a determine period to ensure sufficient binding of the antigens on the respective specific antibodies attached to surfaces (A) and (B). This incubation time was an accurately measured 10 min period in the course of which the amount of overall bound antigen was in proportion to its concentration in the standard. Tests against blanks (zero % of antigen reagents) were run identically.

Thereafter, the cells were emptied and rinsed of all unbound materials and a combined solution of second antibodies to the antigents attached to the waveguide surface was added. This combination solution contained 1/40 (v/v) buffer diluted rabbit anti-HSA and rabbit anti-IgG (obtained from DAKO IMMUNOGLOBULINS) labelled with fluorescein (fluorescein isothiocyanate, FITC was used as the actual marker according to usual means).

One the fluorescent labelled mixed antibody solution was added, an instantaneous fluorescence rise was observed at the output of the waveguide followed by a slower rate dependent siganl (see FIG. 9) whose height after a given period was in proportion to the standard concentrations in IgG and HSA taken independently. After decoding, the signals components originating from surfaces (A) and (B) were displayed separately and the results are gathered in the following table.

| Concentration of IgG and HSA in standards (ng/ml) | Response from surface A (arbitrary units) | | | Response from surface B (arbitrary units) | | |
|---|---|---|---|---|---|---|
| | Test | repeat | average | Test | repeat | average |
| 0.1 | 1 | 2 | 1.5 | −1 | 2 | 1 |
| 1.0 | 27 | 24 | 25 | 44 | 44 | 44 |
| 10.0 | 64 | 61 | 62 | 60 | 56 | 58 |
| 100.0 | 160 | 170 | 165 | 140 | 135 | 137 |

Figure 9:
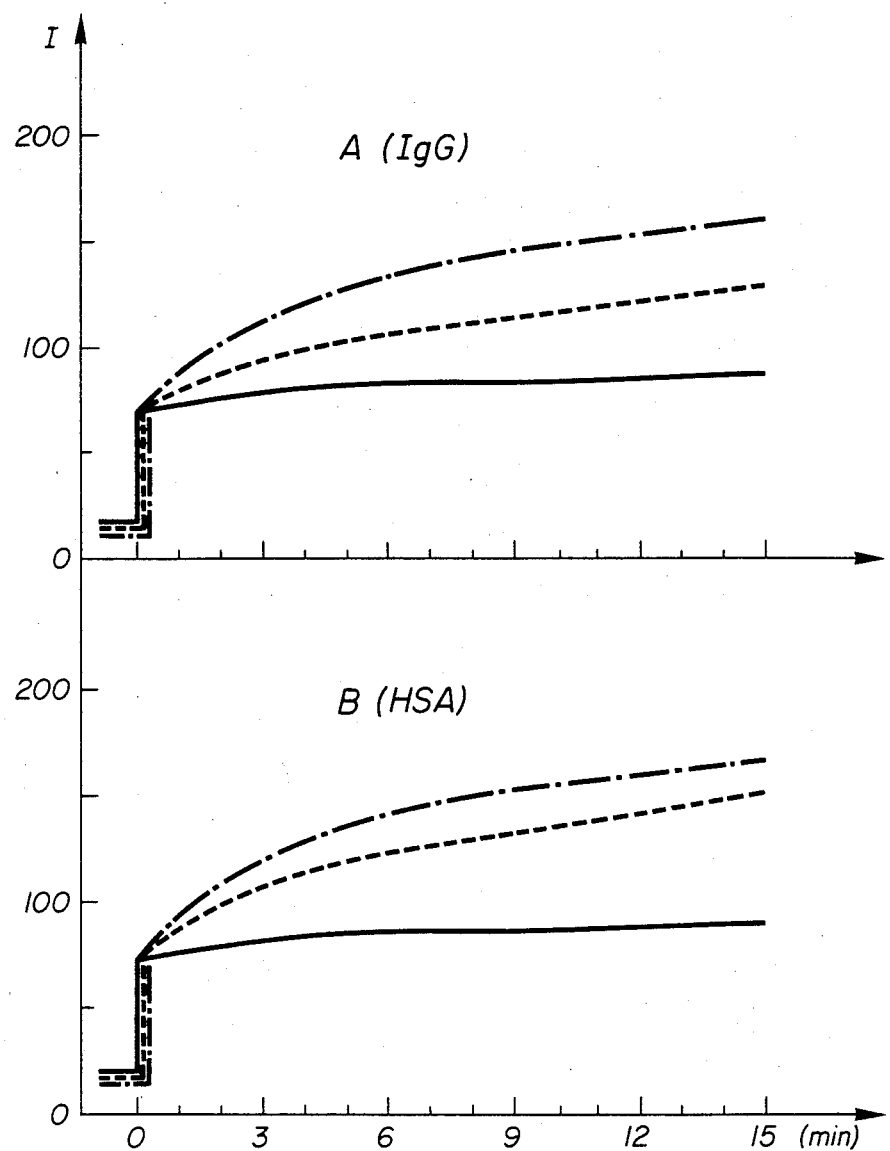
FIG. 9 illustrates another type of analysis involving fluorescence.

FIG. 9 shows graphically for components A and B the situation from zero to 15 min in the case of the 1 $\mu$g/l (dashed line) and 10 $\mu$g/l (mixed line) standards. The full line represents blanks.

As in the previous Example, samples with unknown concentrations of IgG and HSA were run identically and ascertained by comparing with the standards.

We claim:

1. A method of determining the presence of more than one component in a single liquid sample by use of multiple internal reflections of excitation radiation in a waveguide comprising the steps of:
   coating a surface of a waveguide with a reactant specific to a first component contained in the sample;
   exposing said coated surface to the sample, thereby allowing formation of a layer of a complex formed by the reaction of said reactant and said first component;
   illuminating an input end of said waveguide with an optical excitation signal in a manner such that an evanescent component of said signal penetrates a sufficient distance into said sample to interact with said complex layer with a second component in the bulk of said sample;
   collecting the optical signal after said interaction; and
   subsequently analyzing said signal to determine the presence or quantity of each of said first and second components in the sample.

2. The method of claim 1 wherein said signal interaction results from absorption, scattering or the generation of fluorescence.

3. The method of claim 2 wherein the excitation signal interacts with said complex layer during the formation thereof so as to provide a time dependent response on said first component and an instant response on said second component.

4. The method of claim 2 wherein said waveguide is an optical slide or an optical fiber.

5. The method of claim 1 for substantially simutaneously determining in a blood sample total hemoglobin and further hemoglobin factors or derivatives thereof relative to said total hemoglobin, the method comprising:
   (a) Coating at least part of the surface of an optical waveguide system of a refractive index greater than that of the sample with one or more coatings of complexing reactants, each coating being of a reactant specific to that factor or derivative of hemoglobin and capable of building up a layer of said complex upon reaction with said hemoglobin factor or derivative;
   (b) Illuminating said waveguide at an input end with a beam of light and collecting the exiting light at an output end, said beam being transmitted along said guide by a multiple internal reflection mechanism at an angle such that the effective range of action outside the guide of an evanescent light component associated with said beam exceeds that of said complex layer;
   (c) Contacting together said blood sample and said illuminated waveguide whereby, on one hand, part of the light traveling in the guide is initially absorbed by interaction of the evanescent wave component with the hemoglobin of the bulk sample, this resulting in an instantaneous sharp dip (I) in the exiting light from said output end and, on the second hand, an immuno-type reaction develops between said glycosylated hemoglobin or other factor in said blood sample and corresponding reactant on the waveguide with consecutive build-up of said complex layer, such build up resulting in a relatively slower change of signal of said exiting light, said relatively slower change of signal being due to the interaction of said evanescent wave component with said complex layer in formation;
   (d) Observing, measuring and/or recording said sudden optical absorption drop (I) occurring to the transmitted light collected from said output end, said measured drop being quantitatively related with the concentration of the total hemoglobin of the sample;
   (e) Observing, measuring and/or recording said relatively lower change, the magnitude (M) and rate (K) of which quantitatively relates to the amount of glycosylated hemoglobin or other factor in the sample;
   (f) Effecting the required computations to express the results obtained from the values of I and M or K in terms of concentration of total hemoglobin and/or ratio of glycosylated hemoglobin or other factor to hemoglobin in the sample.

6. The method of claim 5, wherein the steps (d) and (e) are both effected on the signal resulting from the interaction of the incident light and the sample at the area of the waveguide bearing the reactant coated thereon.

7. The method of claim 5 wherein the blood factor determined is glycosylated hemoglobin.

8. The method of claim 5, wherein step (d) is effected on the component of the output signal resulting from said interaction on a part of the waveguide not coated with the reactant.

9. The method of claim 8, wherein there is used a dual type waveguide, one portion of which is coated with reactant and another portion of which is not coated with reactant.

10. The method of claim 9, wherein said other portion is coated with a blocking protein for minimizing the possible deposition of hemoglobin on the waveguide uncoated surface area.

11. The method of claim 9, which comprises using as a dual waveguide an analytical cuvette whose main opposite walls are light conductive and made of a transparent material of suitable refractive index greater than that of the blood sample, this material serving as the waveguide.

12. A method determining the presence of more than one component in a single liquid sample by use of multiple internal reflections of excitation radiation in a waveguide, said method comprising the steps of:
   coating a first surface of said waveguide with a reactant specific to a first component in said sample;
   exposing said first coated surface, and a second surface of said waveguide, to said sample thereby allowing formation of a layer of complex on the first surface, said layer formed by the reaction of said reactant and said first component;
   illuminating an input and of said waveguide with an optical excitation signal in a manner such that the evanescent component of said signal interacts with said complex layer at said first surface, and with the bulk solution of said sample at said second surface;
   collecting the optical signal after said interactions; and
   subsequently processing said signal to ascertain the presence or quantity of each of said first and second components.

13. The method of claim 12 wherein the first and second surfaces are part of separately illuminated waveguide elements.

14. The method of claim 12 wherein said collecting step further comprises separating the effect from each interaction by separating the signal as to wavelength.

15. The method of claim 12 wherein the first and second surfaces are alternately exposed to the excitation signal.

16. An apparatus for the combined determination of hemoglobin and at least one hemoglobin factor in a blood sample comprising waveguide means for carrying an optical signal;

light source means for providing said optical signal to an input end of said waveguide means;

holding means for containing said blood sample;

light detecting means for collecting said optical signal exiting from an output end of said waveguide means, and for generating an electrical signal in response to said optical signal; and computing means for processing said electrical signal and for providing output information in response thereto;

wherein the waveguide means is coated along a portion thereof with a reactant specific to a hemoglobin factor so as to form a layer of complex from said reactant and said factor when said waveguide is exposed to said sample; and wherein a second portion of said waveguide means is untreated or treated with a hemoglobin factor blocking agent;

so that when the light signal interacts with said reactant coated portion, information is gathered for the determination of a hemoglobin factor, and where the light signal interacts with said untreated or blocked portion, information is gathered for the determination of hemoglobin.

17. The apparatus of claim 16, wherein the waveguide means has a dualtype structure and comprises two independent optical elements to simultaneously or alternately carry said optical signal, one of said elements being reactant coated and the other being bare or blocked.

18. The apparatus of claim 17, in which said light source means comprise two independent alternately flashing light sources the output of which is focussed each on one optical end of said elements via beam splitting means and in which the other end of said elements is made totally reflective so that the light signal carried by said elements travels forwards and backwards therein.

19. The apparatus of claim 17, using as the waveguide means an optical cell or cuvette of which two oppositely facing walls operate as said waveguide elements.

20. The apparatus of claim 19, in which said light source means comprises chopper means to alternately inject the signal light into the two elements of the dual-waveguide.

21. The apparatus of claim 20, in which said chopper means are either a rotating mirror or a chopper disk.

22. An apparatus for the substantially simultaneous determination in more than one component of a liquid sample comprising:

waveguide means for carrying an optical signal;

light source means for providing said optical signal to an input end of said waveguide means;

holding means for containing said liquid sample;

light detecting means for collecting said optical signal from an output end of said waveguide means, and for generating an electrical signal in response to said optical signal;

computing means for processing said electrical signal and providing output information in response thereto;

wherein said waveguide means is coated along a portion thereof with a reactant specific to a first component in said sample so as to form a layer of complex from said reactant and said component when said waveguide is exposed to said sample; and wherein said light source means and said waveguide means are arranged such that an evanescent component of said light source means interacts with both said reactant/component complex and the bulk of said sample so that information is obtained substantially simultaneously from each both the reactant/component complex and the bulk of said sample.

* * * * *